United States Patent
Matsumoto et al.

(10) Patent No.: US 11,105,555 B2
(45) Date of Patent: Aug. 31, 2021

(54) METHOD FOR MANUFACTURING FREEZE-DRIED BODY AND MANUFACTURING DEVICE FOR SAME

(71) Applicant: NITTO DENKO CORPORATION, Osaka (JP)

(72) Inventors: Chie Matsumoto, Osaka (JP); Takao Yoshikawa, Osaka (JP); Takuya Shishido, Osaka (JP); Yuji Toyota, Osaka (JP); Sachiko Sakamoto, Osaka (JP); Yoshimitsu Shimomura, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 44 days.

(21) Appl. No.: 16/499,482

(22) PCT Filed: Apr. 2, 2018

(86) PCT No.: PCT/JP2018/014090
§ 371 (c)(1),
(2) Date: Sep. 30, 2019

(87) PCT Pub. No.: WO2018/186343
PCT Pub. Date: Oct. 11, 2018

(65) Prior Publication Data
US 2020/0025443 A1    Jan. 23, 2020

(30) Foreign Application Priority Data
Apr. 4, 2017  (JP) .............................. JP2017-074713

(51) Int. Cl.
*F26B 5/04* (2006.01)
*A23L 3/44* (2006.01)
(Continued)

(52) U.S. Cl.
CPC ................ *F26B 5/048* (2013.01); *A23L 3/44* (2013.01); *A23L 3/54* (2013.01); *F26B 5/06* (2013.01); *A61K 9/19* (2013.01)

(58) Field of Classification Search
CPC .... F26B 5/048; F26B 5/06; A23L 3/44; A23L 3/54; A61K 9/19
(Continued)

(56) References Cited

U.S. PATENT DOCUMENTS 3,313,032 A * 4/1967 Malecki .................. F26B 5/065
                                                       34/288
4,608,764 A * 9/1986 Leuenberger ............. F26B 3/08
                                                       34/295
(Continued)

FOREIGN PATENT DOCUMENTS

CN    105585761 A        5/2016
EP    3222952 B1 *  1/2019  ................ F26B 5/06
(Continued)

OTHER PUBLICATIONS

Office Action issued in CN Patent Application No. 201880023459.X dated Jun. 1, 2020, along with a machine English language translation.

(Continued)

*Primary Examiner* — Stephen M Gravini
(74) *Attorney, Agent, or Firm* — Greenblum & Bernstein, P.L.C.

(57) ABSTRACT

The present invention aims to provide a method and an apparatus for producing a lyophilized body, each of which can achieve energy saving, low cost, and a reduction in processing time and can provide a lyophilized body less damaged by a freezing process and a drying process. The present invention relates to a method for lyophilizing a substance using an electromagnetic wave, and the lyo-
(Continued)

philization method includes freezing the substance under irradiation of at least an electromagnetic wave and reduced-pressure drying the frozen substance under irradiation of at least an electromagnetic wave.

15 Claims, 1 Drawing Sheet

(51) Int. Cl.
*A23L 3/54* (2006.01)
*F26B 5/06* (2006.01)
*A61K 9/19* (2006.01)

(58) Field of Classification Search
USPC .......................................................... 34/245
See application file for complete search history.

(56) References Cited

U.S. PATENT DOCUMENTS

| | | | |
|---|---|---|---|
| 6,250,087 B1 | 6/2001 | Owada et al. | |
| 6,584,782 B2* | 7/2003 | Leuenberger | F26B 3/08 |
| | | | 62/64 |
| 6,723,347 B1 | 4/2004 | Yamagata et al. | |
| 7,836,606 B2* | 11/2010 | Gehrmann | F26B 5/065 |
| | | | 34/284 |
| 8,516,714 B2* | 8/2013 | Biemans | A61K 9/19 |
| | | | 34/284 |
| 9,046,303 B2* | 6/2015 | Yagi | F26B 5/06 |
| 10,465,985 B2* | 11/2019 | Ganguly | F26B 5/065 |
| 10,670,336 B2* | 6/2020 | Corver | F26B 5/06 |
| 10,809,003 B2* | 10/2020 | De Beer | F26B 5/06 |
| 2002/0076821 A1 | 6/2002 | Beck et al. | |
| 2004/0086420 A1* | 5/2004 | MacPhee | A61L 2/0047 |
| | | | 422/22 |
| 2005/0008634 A1 | 1/2005 | Cohen-Vered et al. | |
| 2006/0137212 A1 | 6/2006 | Nomine | |
| 2013/0177594 A1 | 7/2013 | Shishido et al. | |
| 2016/0157501 A1 | 6/2016 | Monckeberg | |
| 2018/0017324 A1 | 1/2018 | Sun et al. | |
| 2020/0025443 A1* | 1/2020 | Matsumoto | F26B 5/048 |
| 2020/0268806 A1* | 8/2020 | Reems | A61K 35/28 |
| 2020/0306757 A1* | 10/2020 | Lee | B01L 3/50273 |
| 2020/0330573 A1* | 10/2020 | Tan | C12N 1/20 |
| 2020/0333333 A1* | 10/2020 | Ellinger | G01N 33/54313 |

FOREIGN PATENT DOCUMENTS

| | | | | |
|---|---|---|---|---|
| EP | 3303958 B1 * | 10/2019 | | A23L 3/44 |
| JP | 2002-333250 A | 11/2002 | | |
| JP | 2004-081134 A | 3/2004 | | |
| JP | 2006-177640 | 7/2006 | | |
| JP | 2006-517540 A | 7/2006 | | |
| JP | 2009-137993 | 6/2009 | | |
| JP | 2013-142077 A | 7/2013 | | |
| JP | 5439655 B1 | 3/2014 | | |
| JP | 2016-527468 A | 9/2016 | | |
| JP | WO2018186343 A1 * | 2/2020 | | A23L 3/44 |
| JP | 6718888 B2 * | 7/2020 | | F26B 3/28 |
| KR | 10-2007-0095942 | 10/2007 | | |
| WO | 01/021187 A1 | 3/2001 | | |
| WO | 01/24647 A1 | 4/2001 | | |
| WO | 2004/064787 A2 | 8/2004 | | |
| WO | WO-2013036107 A2 * | 3/2013 | | F26B 5/06 |
| WO | 2016/138790 A1 | 9/2016 | | |
| WO | WO-2016196110 A1 * | 12/2016 | | A23L 3/44 |
| WO | WO-2018186343 A1 * | 10/2018 | | F26B 5/048 |

OTHER PUBLICATIONS

Extended European Search Report issued in EP Patent Application No. 18780389.5, dated Dec. 21, 2020.
Woo et al., "Effects of Electric and Magnetic Field on Freezing and Possible Relevance in Freeze Drying", *Drying Technology*, vol. 28, pp. 433-443 (2010).
International Search Report issued in PCT/JP2018/014090, dated Jul. 3, 2018, along with an English-language translation.
International Preliminary Report on Patentability issued in PCT/JP2018/014090, dated Oct. 8, 2019, along with an English-language translation.
Chinese Office Action received in counterpart CN Application. No. 201880023459.X, dated Apr. 23, 2021, and English language translation thereof.

* cited by examiner

FIG.1

FIG.2

METHOD FOR MANUFACTURING FREEZE-DRIED BODY AND MANUFACTURING DEVICE FOR SAME

TECHNICAL FIELD

The present invention relates to methods and apparatuses for producing a lyophilized body. In particular, the present invention relates to a method for producing a lyophilized body including a freezing process and a drying process each of which is performed under irradiation of a magnetic field and an electromagnetic wave and relates to an apparatus for producing a lyophilized body.

BACKGROUND ART

A lyophilization technique is widely used in production of products such as foods and pharmaceuticals. It is a process of removing most of the water in these materials to preserve materials classified as foods, pharmaceuticals, or other products. The lyophilization technique is also called "freeze-drying" and is achieved by freezing a substance and heating the frozen substance under reduced pressure to sublimate frozen water in the substance into vapor.

To sublimate frozen water in the substance under reduced pressure, heat of sublimation needs to be supplied. An example of a method for supplying heat of sublimation is convection heating, which however exhibits a relatively low heating effect because the amount of the gas molecules surrounding the substance is relatively small under reduced pressure. Instead, conductive heating has often been used in conventional lyophilization processes. In usual conduction heating, a substance is placed in contact with a heated surface and is heated from the outside to the inside of the substance by conduction energy. Thus, heating of the inside depends on conduction heat transfer.

This method has a problem that the contact surface may become an insulator having high insulation as the contact surface dries. This gradually prevents heat from being transferred into the substance. Furthermore, if the contact surface or heated surface is overheated before completion of the sublimation of water in the substance, the substance may be damaged. For this reason, the amount of conductive heat supplied during the lyophilization process needs to be carefully controlled. Under this restricted conditions, a conventional lyophilization process may take a great deal of time. For example, the lyophilization of fruits or vegetables in a conventional manner typically takes 8 to 40 hours, depending on the shape, type, and amount of the substance agricultural product. Here, the substance may be damaged when its outside is overheated, and thus, acceleration of the lyophilization process by simply increasing the amount of heat should be avoided. Overheating in the drying stage may also cause deterioration of the food quality such as a flavor, vitamin content, or antioxidant content; and similarly, deterioration of the drug quality such as a flavor, vitamin content, or antioxidant content; and denaturation of drugs and additives.

For example, Patent Literature 1 proposes a simple process for producing a protein powder which includes freezing a protein-containing solution at a cooling speed of about −300° C. to −10° C./min, and then drying. This process can provide a stable protein powder which retains a higher-order structure. Patent Literature 2 proposes a pharmaceutical composition obtained by lyophilizing a solution containing a drug and a stabilizer which is a combination of a specific sugar, a specific polysaccharide, and a specific edible polymer. When a lyophilization technique is used in the pharmaceutical field, the production method and/or additives need to be examined so as to provide stable preparations.

Convection heating or conduction heating included in a conventional lyophilization technique consumes a large amount of energy. In order to achieve energy saving and low cost, a technique that can shorten the processing time has been required.

In a recent known technique in the food field, a static magnetic field and an electromagnetic wave are used in freezing to control the size of ice crystals in cells or the like of a material to be frozen. This technique achieves better freezing conditions without breaking the cellular structure in the material to be frozen (Patent Literature 4: JP 5439655 B, Patent Literature 5: WO 01/024647). Also proposed is use of an electromagnetic wave such as a microwave in drying in a lyophilization process. The electromagnetic energy differs from the conduction energy in that it passes through the outer layer of the material and heats the inside thereof, which increases the sublimation rate of water in the material. In other words, use of microwave energy, which is electromagnetic energy, can effectively supply heat of sublimation required for drying, and can reduce the length of drying time and the amount of energy (Patent Literature 3: JP 2016-527468 A). Conventional lyophilization techniques do not use such freezing using a static magnetic field and an electromagnetic wave as described above. This is because if ice crystals in the frozen material are small, the ice is less likely to sublime in the subsequent drying step, which is undesirable from the viewpoint of energy saving, low cost, and a reduction in processing time (Non-Patent Literature 1).

CITATION LIST

Patent Literature

Patent Literature 1: WO 01/021187
Patent Literature 2: JP 2013-142077 A (lyophilized preparation containing stabilizer)
Patent Literature 3: JP 2016-527468 A
Patent Literature 4: JP 5439655 B
Patent Literature 5: WO 01/024647

Non-Patent Literature

Non-Patent Literature 1: M. W. Woo and A. S. Mujumdar Technology, 28: 433-443, 2010

SUMMARY OF INVENTION

Technical Problem

In view of the current state of the art described above, the present invention aims to provide a method and an apparatus for producing a lyophilized body, each of which can achieve energy saving, low cost, and a reduction in processing time and can provide a lyophilized body less damaged by a freezing process and a drying process.

Solution to Problem

The present inventors have intensively studied to solve the above problems and have found that a lyophilization method in which both the freezing and the reduced-pressure drying are performed under irradiation of an electromagnetic wave is superior to a conventional lyophilization method in terms of reducing the production processing time. They also found that the lyophilized body obtained by this production method has a lower water content, better stability, and better quality than that obtained by a conventional lyophilization method. Thereby, the present invention has been completed.

That is, the present invention relates to a method for producing a lyophilized body, including:

freezing a substance that is a raw material of the lyophilized body under irradiation of at least an electromagnetic wave; and reduced-pressure drying the frozen substance under irradiation of at least an electromagnetic wave.

The freezing is preferably performed under irradiation of an electromagnetic wave and a magnetic field, and the reduced-pressure drying is preferably performed under irradiation of an electromagnetic wave and a magnetic field.

The reduced-pressure drying preferably includes primary reduced-pressure drying and secondary reduced-pressure drying.

The magnetic field is preferably a static magnetic field.

The substance is preferably a drug-containing material containing water and at least one drug.

The at least one drug preferably includes a protein.

The protein is preferably a physiologically active protein.

The physiologically active protein is preferably at least one selected from the group consisting of an antibody protein, an antigen protein, and an allergenic protein.

The present invention also relates to a lyophilizer for producing a lyophilized body, the lyophilizer including:

a freezing means configured to freeze a substance that is a raw material of the lyophilized body;

a pressure reducing means configured to reduce an ambient pressure around the frozen substance; and an electromagnetic wave generating means configured to generate an electromagnetic wave to be applied to the substance.

The lyophilizer preferably further includes a magnetic field generating means configured to generate a magnetic field to be applied to the substance.

The magnetic field generating means is preferably a static magnetic field generating means configured to generate a static magnetic field.

The present invention is described in detail below.

The present invention relates to a method for producing a lyophilized body including freezing a substance that is a raw material of the lyophilized body under irradiation of at least an electromagnetic wave; and reduced-pressure drying the frozen substance under irradiation of at least an electromagnetic wave.

The lyophilization method in the present invention may be any conventional lyophilization method. For example, the freezing method may be air-blast freezing (air freezing), liquid freezing, contact freezing, or liquefied gas freezing, with air-blast freezing or contract freezing being preferred. The drying method is preferably reduced-pressure drying (vacuum drying) as in the conventional lyophilization method.

The frequency of the electromagnetic wave to be applied may be the same throughout the freezing and the reduced-pressure drying in the present invention, or may be at least partly varied in these processes. Further, the frequency of the electromagnetic wave to be applied may be the same in the early stage, the middle stage, and the late stage of the reduced-pressure drying, or may be varied among these stages. The reduced-pressure drying may include a time during which no electromagnetic wave is applied.

An electromagnetic wave may be applied to the substance using, for example, an electromagnetic wave generating means mainly composed of an electromagnetic wave oscillator that generates an electromagnetic wave pulse, an amplifier, and an electromagnetic wave emitting antenna. In the present invention, the structure of the electromagnetic wave generating means is not limited to this structure, and any known electromagnetic wave generating means may be used.

The freezing and the reduced-pressure drying in the present invention may be performed under irradiation of an electromagnetic wave and a magnetic field.

The magnetic field in the present invention may be a static magnetic field or a pulse magnetic field, with a static magnetic field being preferred in terms of convenience.

The static magnetic field refers to a magnetic field whose magnetic field intensity does not change with time. The static magnetic field may be applied using any means, and may be applied, for example, using a magnet or a magnetic head produced by a semiconductor process, or by flowing an electric current to microcoils. In terms of cost, preferred is use of a permanent magnet such as an alnico magnet, a ferrite magnet, a samarium magnet, or a neodymium magnet. A ferrite magnet is particularly preferred because it is inexpensive, has high magnetic permeability, and is usable for various applications.

The electromagnetic wave in the present invention refers to a non-ionizing radiation having a frequency band of about 1 Hz to 1 THz. The non-ionizing radiation may be, for example, so-called a microwave such as a millimeter wave, centimeter wave, or ultrashort wave.

In the freezing in the present invention, the substance is frozen by lowering the temperature of the substance from room temperature (25° C.) to the temperature range of −80° C. to −20° C. under irradiation of an electromagnetic wave having a predetermined frequency. The freezing temperature is preferably −40° C. to −70° C., more preferably −60° C. The freezing may be performed under a magnetic field in addition to an electromagnetic wave.

At least part of the freezing may be performed under irradiation of an electromagnetic wave and/or a magnetic field to the substance. The freezing may include a time during which an electromagnetic wave and/or a magnetic field are/is not applied to the substance.

In the reduced-pressure drying in the present invention, the ambient pressure around the frozen substance is reduced to a pressure at which sublimation can occur, and the ambient temperature around the substance increases to a temperature at which sublimation can occur, and then the frozen substance is dried under irradiation of an electromagnetic wave having a certain frequency so as to sublimate frozen water in the substance.

In the case of reducing the ambient pressure around the substance, the ambient pressure may be reduced in a vacuum chamber containing the frozen substance by reducing the pressure in the vacuum chamber. In the reduced-pressure drying, the primary reduced-pressure drying and the secondary reduced-pressure drying may be in the same or different reduced pressure states and may be in the same or different temperature states. Furthermore, the drying of the substance can be accelerated by increasing the ambient temperature around the substance, in the primary reduced-pressure drying, to a temperature at which the frozen state can be maintained, and then, in the secondary reduced-pressure drying, to a temperature not lower than 0° C. at which no quality problem of the substance occurs.

The freezing and the reduced-pressure drying each may be performed using a lyophilization chamber or they may be performed using different means. For example, the freezing and the reduced-pressure drying may be performed using a freezing chamber and a vacuum chamber, respectively. To reduce the size of the lyophilizer, a lyophilization chamber is preferably used.

In the reduced-pressure drying, a heater or other structures used in a conventional lyophilizer may be used to increase the ambient temperature around the substance from the freezing temperature to the reduced-pressure drying temperature.

The reduced-pressure drying may be performed under irradiation of a magnetic field in addition to an electromagnetic wave. At least part of the reduced-pressure drying may be performed under irradiation of an electromagnetic wave and/or a magnetic field to the substance. The reduced-pressure drying may include a time during which an electromagnetic wave and/or a magnetic field are/is not applied to the substance.

The electromagnetic wave generating means used to apply an electromagnetic wave to the substance may include a control means configured to control the electromagnetic wave output. The expression "control the electromagnetic wave output" means that the electromagnetic wave output is controlled according to a decrease in the mass of the substance by controlling the "output (e.g., wattage) per unit mass (e.g., kilogram)" of the electromagnetic wave to be applied to the substance. The control of the electromagnetic wave output enables, for example, efficient supply of heat of sublimation as the mass of the substance changes with the progress of the reduced-pressure drying (sublimation of ice).

The electromagnetic wave may be applied continuously or intermittently in the reduced-pressure drying.

The reduced-pressure drying may be composed of two stages of the primary reduced-pressure drying and the secondary reduced-pressure drying. In the primary reduced-pressure drying, the highest electromagnetic wave output that can be applied to the substance without causing an overheated point is determined, and the determined high electromagnetic wave output is applied, and the secondary reduced-pressure drying may be performed under irradiation of an electromagnetic wave whose output is controlled according to the decrease in the mass of the substance. The secondary reduced-pressure drying may also be performed under irradiation of an electromagnetic wave whose output is sufficiently lowered to prevent overheating of the substance due to the very low water content of the substance or may be performed under no irradiation of an electromagnetic wave.

To achieve uniform distribution of heat in the substance, the application of an electromagnetic wave may be intermittent by interposing a predetermined time during which no electromagnetic wave output is applied.

The electromagnetic wave generating means may include a temperature determination means configured to determine whether the temperature of the frozen substance exceeds a set temperature. After most of the ice crystals in the substance sublimate, the substance is likely to be thermally damaged. To avoid thermal damage of the substance, the electromagnetic wave output is preferably controlled to be low according to the determination whether the temperature of part or the whole of the substance has reached a temperature exceeding the set temperature. In order to detect overheated points locally present in the substance, the temperatures of multiple points may be monitored by the temperature determination means.

In the reduced-pressure drying in the present invention, the set temperature may be within the range of −60° C. to 0° C. The set temperature may be the threshold temperature. The threshold temperature can be depending on the equilibrium temperature. For example, when the equilibrium temperature is −20° C. in the early stage (primary reduced-pressure drying) in the reduced-pressure drying, a local temperature of 0° C. may highly possibly cause thermal runaway at this point. On the other hand, when the equilibrium temperature increases in the late stage (secondary reduced-pressure drying) in the reduced-pressure drying, the local temperature may be 0° C. in some cases. Accordingly, the threshold temperature may be determined from the difference of the equilibrium temperature of the substance, may be a constant value, or may be calculated by other methods.

The set temperature may be determined based on any of the properties of the substance, the elapsed time of the processing, the time desired for the reduced-pressure drying, and the features desired for the final lyophilized body. For example, when the substance is a drug-containing material containing water and at least one drug, the set temperature of the primary reduced-pressure drying is preferably within −40° C. to −10° C., more preferably −20° C. Further, the set temperature of the secondary reduced-pressure drying is preferably within 10° C. to 35° C., more preferably within 20° C. to 30° C.

The temperature may be monitored, for example, by an infrared camera for electromagnetic wave use.

When the substance that is a raw material of the lyophilized body is frozen under irradiation of an electromagnetic wave, free water (water molecules) in the substance vibrates continuously, inhibiting the growth of ice crystals and producing fine ice crystals. Thereby, the substance can be frozen without excessive breakage of cell structures or other structures.

Further, water molecules in the substance are aligned in the direction of the magnetic field by application of a magnetic field in the freezing, and are directed to the N pole or the S pole. The number of the water molecules directed to the N pole and the number of the water molecules directed to the S pole are not equal to each other. The difference between the numbers generates a net magnetic field, and further, the precession motion of the water molecules occurs around the axis in the direction of the applied magnetic field. This also inhibits the growth of ice crystals, and finer ice crystals can be produced by application of a magnetic field together with an electromagnetic wave. Thus, breakage of cell structures or other structures can be prevented. When the magnetic field is a static magnetic field, water molecules in the substance are almost uniformly arranged at predetermined intervals in the unidirectional and substantially-uniform magnetic field. These water molecules vibrate when an electromagnetic wave is applied in such a state, producing fine ice crystals at predetermined intervals.

In the reduced-pressure drying of the frozen substance under irradiation of an electromagnetic wave, an electromagnetic wave is applied to the respective ice crystals dispersed in the substance, which promotes the excitation of ice molecules and generates heat. Here, ice molecules are less likely to vibrate as freely as water molecules. When the frozen substance in which part of water in the substance is in the form of water molecules and the rest thereof is in the form of ice crystals is subjected to reduced-pressure drying, water molecules absorb more energy than ice molecules and are undergone rapid temperature rise. If the substance cannot sufficiently and rapidly release this heat, the substance is overheated and may be partly damaged. On the other hand, in the present invention, the frozen substance contains fine ice crystals as described above, and the fine ice crystals are almost uniformly sublimated by application of an electromagnetic wave. This can prevent damage due to overheating and can achieve sufficient and uniform drying of the substance even if the drying time is shortened.

Accordingly, lyophilization can be completed without impairing the inherent properties of the substance (e.g., texture, appearance, or nutrients of foods, and drug activities of drugs).

The substance that is a raw material of the lyophilized body in the present invention may be, but is not limited to, foods including fresh foods such as meat, fish, vegetables, and fruits, processed foods, functional foods, drugs, pharmaceuticals, quasi-drugs, cosmetics containing natural ingredients, and mixtures of these with water. In particular, the substance is preferably a drug-containing material containing water and at least one drug.

The drug(s) contained in the substance that is a raw material of the lyophilized body in the present invention may be any biologically or pharmacologically active component, and is preferably one suitable for lyophilization. Examples include various peptides, proteins, DNAs, RNAs, siRNAs, polysaccharides, lipopeptides, lipoproteins, lipopolysaccharides, low-molecular-weight compounds, antibodies, antigens, toxins, and vaccines, such as physiologically active polypeptides, antipyretics, analgesics, anti-inflammatory drugs, antipodagrics, therapeutic drugs for hyperuricemia, hypnotics, sedatives, sleep inducers, anxiolytics, antiepileptics, antipsychotics, antidepressants, antimaniac drugs, antiparkinsonian drugs, drugs for non temper tantrums, opioid agonists, therapeutic agents for asthma, anesthetics, antiarrhythmic drugs, therapeutic agents for arthritis, anticonvulsants, ACE inhibitors, decongestants, antibiotics, autonomic drugs, cerebral circulation and metabolism improvers, allergy medications, antianginal drugs, β-blockers, calcium antagonists, cardiotonic drugs, delivery accelerating drugs, diuretics, antihypertensives, vasoconstrictors, vasodilators, therapeutic agents for hyperlipidemia, vasopressors, bronchodilators, drugs for peptic ulcer, stomachics, digestants, laxatives, intestinal drugs, antacids, diabetes drugs, hormone preparations, vitamin preparations, osteoporosis drugs, antimicrobials, chemotherapeutic agents, antitumor agents, muscle relaxants, anticoagulants, hemostatics, antituberculosis drugs, narcotic antagonists, bone resorption inhibitors, angiogenesis inhibitors, central nervous system drugs, anti-vertigo drugs, drugs for circulatory organs, respiratory stimulants, antidiarrheal drugs, cholagogues, drugs for digestive organs, drugs for urinary organs, drugs for liver diseases, antihypertensives, antihypotensives, immunosuppressants, immunomodulators, antiemetics, antiinfective drugs, antineoplastic drugs, antifungals, antivirals, antidiabetics, antiallergic agents, antihistamines, antipruritics, bone regulators, cardiovascular drugs, hypocholesterolemic agents, antimalarials, pharmaceutical agents for ceasing smoking, antitussives, expectorants, mucolytics, nasal decongestants, dopamine agonists, drugs for digestive tract, neuromuscular blockades, parasympathomimetics, prostaglandins, stimulants, appetite suppressants, thyroid drugs, antithyroid drugs, anti-migraine drugs, anti-obesity drugs, and anti-inflammatory drugs.

These drugs may be used alone or in combination or two or more.

Non-limiting specific examples of the drugs include insulin, glucagon, leuprolide, growth hormones, parathyroid hormones, calcitonin, vascular endothelial growth factor, erythropoietin, heparin, cyclosporin, oxytocin, tyrosine, enkephalin, thyrotropin releasing hormone, follicle-stimulating hormone, luteinizing hormone, vasopressin, vasopressin analogs, catalase, superoxide dismutase, interleukin II, interferons, colony stimulating factor, tumor necrosis factor, melanocyte stimulating hormone, glucagon-like peptide-1, glucagon-like peptide-2, katacalcin, Cholecystokinin-12, Cholecystokinin-8, exendin, gonadoliberin-related peptide, insulin-like protein, leucine-enkephalin, methionine-enkephalin, leumorphin, neurophysin, copeptin, neuropeptide Y, neuropeptide AF, PACAP-related peptide, pancreatic hormone, peptide YY, urotensin, intestinal peptide, adrenocorticotropic peptide, epidermal growth factor, prolactin, luteinizing hormone releasing hormone (LHRH), LHRH agonist, growth hormone releasing factor, somatostatin, gastrin, tetragastrin, pentagastrin, endorphin, angiotensin, thyrotropin releasing hormone, granulocyte-colony stimulating factor, granulocyte-macrophage-colony stimulating factor, heparinase, antigens for influenza vaccine, tetanus toxins, diphtheria toxins, proteins for cancer vaccine, peptides for cancer vaccine, β-amyloid, immunoglobulins, siRNAs for treatment of cirrhosis, siRNAs for treatment of cancer, low-molecular weight compounds such as bromhexine, granisetron, zolmitriptan, and sumatriptan, and pharmaceutically acceptable salts thereof. Appropriate two or more of these drugs may be used together.

The physiologically active protein has substantially the same biological activity as a physiologically active protein of mammals, in particular humans, and includes naturally-occurring ones and ones obtained by genetic recombination. The protein obtained by genetic recombination includes a protein having the same amino acid sequence as that of natural protein and a protein having an amino acid sequence in which one or more amino acids are delated, substituted, or inserted from/into the same amino acid sequence as that of natural protein and having the biological activity of the natural protein.

Non-limiting examples of the physiologically active protein include antibody proteins such as polyclonal antibodies and monoclonal antibodies, antigen proteins having specific bindings with antibodies, allergenic proteins that cause allergic reactions, lectin proteins, granulocyte colony-stimulating factor (G-CSF), growth hormone, protein hormones such as insulin and prolactin, granulocyte macrophage colony-stimulating factor (GM-CSF), hematopoietic factors such as erythropoietin (EPO) and thrombopoietin, cytokines such as interferons, IL-1 and IL-6, tissue plasminogen activator (tPA), urokinase, serum albumin, blood coagulation factor VIII, leptin, stem cell growth factor (SCF), insulin, parathyroid hormone, growth factor, and enzymes.

Non-limiting examples of the antibody proteins include polyclonal antibodies, monoclonal antibodies, bispecific antibodies, and antibody-like polypeptides, such as chimeric antibodies and humanized antibodies. That is, the antibody proteins may also contain an antibody fragment (antibody-binding fragment) that has an ability to specifically bind to an antigen provided by enzymatic cleavage, peptide synthesis, genetic recombination, or other known techniques, and the antibody as generated can have any isotype.

Examples of the antigen proteins include any immunogenic proteins or peptides that can elicit an immune response against bacteria or viruses.

The allergenic proteins may be any immunogenic proteins or peptides that can specifically react with antibodies from allergy sufferers and elicit an immune response.

Specific examples include allergens derived from pollens of trees (e.g., acacia, alder, ash, American beech, white birch, box elder, mountain cedar, red cedar, cottonwood, cypress, American elm, Chinese elm, Japanese Douglas fir, sweetgum, eucalyptus, hackberry, hickory, American basswood, sugar maple, mesquite, mulberry, oak, olive, pecan tree, pepper tree, pine, privet, Russian olive, American sycamore, tree of heaven, black walnut, and black willow);

allergens derived from pollens of grasses (e.g., cotton, Bermuda grass, Kentucky bluegrass, smooth brome, cultivated corn, meadow fescue, Johnson grass, cultivated oats, orchard grass, redtop, perennial rye grass, rice, sweet vernal grass, timothy, carelessweed, fat hen, common cocklebur, sorrel dock, goldenrod, kochia, lamb's quarters, calendula marigold, nettle, pigweed, English plantain, giant ragweed, short ragweed, western ragweed, Russian thistle, common sagebrush, Scotch broom, and sheep sorrel); allergens derived from insects (e.g., silkworm, mite, honeybee, wasp, ant, and cockroach); allergens derived from fungi (e.g., *Alternaria tenuis, Aspergillus fumigatus, Clostridium botulinum, Candida albicans, Cephalosporium acremonium, Curvularia spicifera, Epicoccum nigrum, Epidermophyton floccosum, Fusarium vasinfectum, Helminthosporium interseminatum, Hormodendrum cladosporioides, Mucor rasemosus, Penicillium notatum, Phoma herbarium, Pullularia pullulans,* and *Rhizopus nigricans*); allergens derived from the skin hair of animals (e.g., dog, cat, and bird); and allergenic proteins derived from house dust; and allergens derived from foods. The allergenic proteins may be any antigen protein that specifically reacts with antibodies from allergy sufferers.

Currently, there is a great demand for hyposensitization therapy for cedar pollen allergy from which many people suffer. Therefore, the allergenic proteins are preferably cedar pollen allergenic proteins.

The cedar pollen allergenic proteins include those containing, as an active ingredient, at least one selected from the group consisting of antigen proteins that are extracted from cedar pollens and specifically react with antibodies from allergy sufferers, and proteins that are highly homologous with these antigen proteins at the amino acid level.

Examples of the antigen proteins extracted from cedar pollens include proteins in cedar pollens which induce the production of cedar pollen-specific IgE antibodies. These proteins in cedar pollens are composed of major cedar pollen allergenic proteins and minor cedar pollen allergenic proteins.

Among these cedar pollen extracts from cedar pollens, those to which a large number of sufferers are sensitive are referred to as major cedar pollen allergenic proteins, and those to which a small number of sufferers are sensitive are referred to as minor cedar pollen allergenic proteins.

The amount of the allergenic protein to be combined with the lyophilized body in the present invention depends on the properties thereof, and is usually preferably $1\times10^{-10}$ to 60% by weight relative to the entire amount of the lyophilized body. A lyophilized body containing less than $1\times10^{-10}$% by weight of the allergenic protein is not suitable for hyposensitization therapy. A lyophilized body containing more than 60% by weight of the allergenic protein leads to remarkably low strength of the lyophilized body in the present invention, which may possibly cause a problem of shape retention.

The drug-containing material in the present invention contains at least one drug and water, and may be in any dosage form such as liquid, gel, or semisolid form. A liquid form and a gel form are preferred, with a liquid form being more preferred. The categories, definitions, properties, production processes, and others of these dosage forms are well known in the technical field. For example, see the Japanese Pharmacopeia, 16th Edition. The material of these dosage forms may be any conventionally known material.

The present invention also relates to a lyophilizer for producing a lyophilized body, the lyophilizer including a freezing means configured to freeze a substance that is a raw material of the lyophilized body, a pressure reducing means configured to reduce an ambient pressure around the frozen substance, and an electromagnetic wave generating means configured to generate an electromagnetic wave to be applied to the substance.

The freezing means and the pressure reducing means may include the structure of the freezing means and the structure of the pressure reducing means in a conventional lyophilizer, respectively.

The lyophilizer may further include a magnetic field generating means configured to generate a magnetic field to be applied to the substance. The magnetic field generating means is preferably a static magnetic field generating means configured to generate a static magnetic field.

The lyophilizer of the present invention also includes a freezing means configured to cool the inside of the lyophilization chamber, a pressure reducing means configured to keep the inside of the lyophilization chamber in a reduced pressure or vacuum, and an electromagnetic wave generating means configured to continuously or intermittently apply an electromagnetic wave having a predetermined frequency to the substance placed at a predetermined position in the lyophilization chamber.

The lyophilizer of the present invention may include in the lyophilization chamber the magnetic field generating means that is disposed so as to sandwich the substance and applies a magnetic field. The magnetic field generating means is preferably a static magnetic field generating means configured to generate unidirectional and substantially uniform magnetic force lines. When the magnetic field generating means is present, the electromagnetic wave generating means is preferably configured to apply an electromagnetic wave to the substance from a direction orthogonal to the magnetic force lines generated from the magnetic field generating means.

Here, the static magnetic field generating means preferably sandwiches the substance in the lyophilization chamber. For example, the static magnetic field generating means has a U-shape or is separately divided into two parts. The magnetic field generating part of the static magnetic field generating means may have any shape and is preferably configured so that the magnetic force lines run substantially linearly in one direction.

The electromagnetic wave generating means is mainly composed of an electromagnetic wave oscillator, an amplifier, and an electromagnetic wave emitting antenna. The electromagnetic wave generating means may also include, as described above, a control means configured to control the output of the electromagnetic wave and/or a temperature determination means configured to detect the temperature of the substance and determines whether the temperature of the substance reaches a predetermined set temperature. The pressure reducing means preferably includes a pressure determination means configured to detect the pressure in the lyophilization chamber and determines whether the pressure reaches a predetermined set pressure so that the pressure in the lyophilization chamber is kept at a predetermined pressure and a control means configured to control the pressure reducing means according to the signals from the determination means.

The lyophilizer preferably includes a temperature control means configured to control the temperature in the lyophilization chamber.

In order to simply produce a drug-containing lyophilized body (hereinafter, also referred to as lyophilized preparation) at low cost, a shelf of a freeze-dryer (freeze-dryer shelf) usually used for lyophilization of injectable preparations of pharmaceuticals may be used. The lyophilizer of the present invention may include a combination of the freeze-dryer and any of the above-described means such as the electromagnetic wave generating means and the magnetic field generating means. Detailed introduction of such a freeze-dryer is described in Masakazu KOBAYASHI, "Drug Production and Freeze-drying Technique" (Iyakuhin seizou to touketu kannsou gijyutsu) (Preparation and Machine (Seizai to Kikai), Nos. 17-23, 25-35 and 38-46). According to the literature, the temperature of the freeze-dryer shelf can be lowered to −70° C. by cooling with common brine. Examples of the freeze-dryer include those available from Kyowa Shinkuu Gijyutsu K. K. (e.g., RL series, RLC series, RLE series, R2L series, R2LW series, and Triomaster series), and those available from Nippon Shinkuu Gijyutsu K. K. (e.g., DF series and DFM series). The freeze-dryer is equipped with a pre-freezer originally designed for use in production of injectable drugs under aseptic and dust-free conditions and is thus suitable for the production of lyophilized preparations. In the case where liquefied gas is used as a primary refrigerant for a freeze-dryer and is introduced through a secondary refrigerant, the temperature of a freeze-dryer shelf can be reduced to a temperature lower than that achieved by normal brine. For example, use of liquid nitrogen as a primary refrigerant and hydrofluoroether (HFE: available from 3M) as a secondary refrigerant can lower the temperature to −135° C. in case of using HFE-7100 (available from 3M) and to −117° C. in case of using HFE-72100 (available from 3M). By using such a method, the drug-containing material can be prevented from direct contact with liquefied gas, and such a difficult problem as the necessity of aseptic and dust-free treatment of liquefied gas can be avoided. Thus, the subsequent drying step can be immediately performed.

The freezing process may be performed on a cooling medium disposed on the freeze-dryer shelf described above. Non-limiting examples of the cooling medium include a plate and a tray. The cooling medium such as a plate or a tray may be flat, uneven, or curved. The cooling medium such as a plate or a tray may be made of any material resistant to a static magnetic field and an electromagnetic wave.

The cooling medium such as a tray may include a mechanism that rotates a substance (e.g., rotatable drum, turntable, or stirrer). When the freezing process and the drying process are performed in the same chamber, this mechanism can provide more uniform distribution of the temperature during drying and can reduce the possibility of damage to the substance due to overheating.

Advantageous Effects of Invention

The method and apparatus for producing a lyophilized body of the present invention each better achieve energy saving, low cost, and a reduction in processing time than conventional lyophilization methods, and also provide a lyophilized body having advantages in maintaining the quality and the appearance without impairing the properties of the substance after lyophilization.

DESCRIPTION OF EMBODIMENTS

The following describes examples of the present invention. The present invention is specifically described with reference to these examples, but is not limited thereto.

Example 1

(Lyophilized Preparation Obtained by Lyophilization Under Irradiation of Electromagnetic Wave)

To purified water (989.9 parts by weight) was dissolved HPC-SSL (an excipient) (Nippon Soda Co., Ltd.) to prepare a 5% HPC-SSL solution. The solution was dispensed in 0.5-mL portions into plastic blister cases (Cryomold (0.5 mL, square), Sakura Finetek). The blister cases were arranged on a shelf plate in a lyophilization chamber. The solutions in each blister case were frozen at −60° C. under irradiation of an electromagnetic wave, dried at −10° C. and 1.5 Pa for 12 hours under irradiation of an electromagnetic wave (primary reduced-pressure drying), and then dried at 30° C. and 1.5 Pa for 4.5 hours under irradiation of an electromagnetic wave (secondary reduced-pressure drying). Thus, a lyophilized preparation was obtained. Each obtained lyophilized preparation portion was quickly put in a dry aluminum pouch and sealed with a heat sealer.

The lyophilization conditions are shown in Table 1 (lyophilization conditions A).

TABLE 1

| Process | Temperature (° C.) | Time (hr) |
| --- | --- | --- |
| Freezing | 25 | 0.5 |
|  | 25 to −60 | 3 |
|  | −60 | 0.5 |
| Primary reduced-pressure drying | −60 to −10 | 2.5 |
|  | −10 | 12 |
| Secondary reduced-pressure drying | −10 to 30 | 1 |
|  | 30 | 4.5 |

Examples 2 to 5

Lyophilized preparations were each obtained by the same procedure as in Example 1, except that the concentration and type of the excipient were changed according to the following Table 2. Each lyophilized preparation portion was put in a dry aluminum pouch and sealed with a heat sealer.

Dextran 70 (Meito Sangyo Co., Ltd.)

Gelatin (Nippi. Inc., product name: Nippi Gelatin SCF)

Pectin (Sansho Co., Ltd., distributed by: P Kelco Japan, product name: GENU pectin type LM-102AS-J)

Comparative Example 1

(Lyophilized Preparation Obtained by Lyophilization Under No Irradiation of Electromagnetic Wave)

A lyophilized preparation was produced under the same conditions as in Example 1, except that the freezing and the reduced-pressure drying were performed under no irradiation of an electromagnetic wave. Each lyophilized preparation portion was put in a dry aluminum pouch and sealed with a heat sealer.

Comparative Examples 2 to 5

Lyophilized preparations were each obtained by the same procedure as in Comparative Example 1, except that the concentration and type of the excipient were changed according to the following Table 2. Each lyophilized preparation portion was put in a dry aluminum pouch and sealed with a heat sealer.

Comparative Example 6

(Lyophilized Preparation Obtained Through Freezing Under Irradiation of Electromagnetic Wave)

A lyophilized preparation was obtained as in Example 1, except that the reduced-pressure drying was performed under no irradiation of an electromagnetic wave. Each lyophilized preparation portion was put in a dry aluminum pouch and sealed with a heat sealer.

Comparative Examples 7 to 10

Lyophilized preparations were each obtained by the same procedure as in Comparative Example 6, except that the concentration and type of the excipient were changed according to the following Table 2. Each lyophilized preparation portion was put in a dry aluminum pouch and sealed with a heat sealer.

Comparative Example 11

(Lyophilized Preparation Obtained Through Reduced-Pressure Drying Under Irradiation of Electromagnetic Wave)

A lyophilized preparation was prepared as in Example 1, except that the freezing was performed under no irradiation of an electromagnetic wave. Each lyophilized preparation portion was put in a dry aluminum pouch and sealed with a heat sealer.

Comparative Examples 12 to 15

Lyophilized preparations were each obtained by the same procedure as in Comparative Example 11, except that the concentration and type of the excipient were changed according to the following Table 2. Each lyophilized preparation portion was put in a dry aluminum pouch and sealed with a heat sealer.

(Method for Evaluating Water Content of Lyophilized Preparation)

The lyophilized preparation was taken out from the aluminum pouch. The water content of the preparation was quickly determined using a Karl Fischer moisture meter. The weight percentage of the water relative to the weight of the preparation was determined as the water content (%) of the lyophilized preparation. The results are shown in Table 2 and the graph in FIG. 1.

Figure 1:
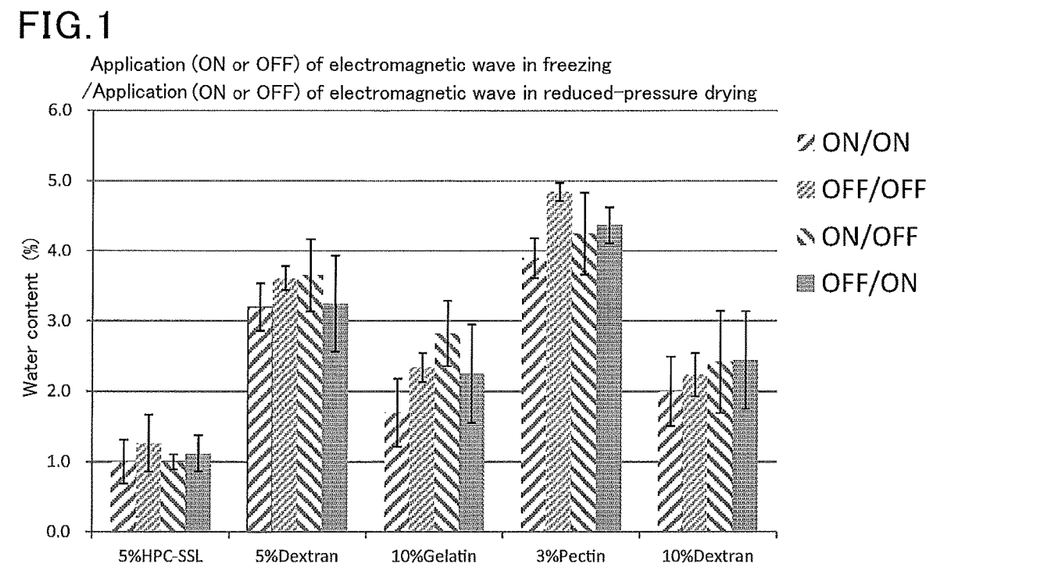
FIG. 1 is a graph visually showing a water content in Examples 1 to 5 and Comparative Examples 1 to 15.

The results shown in Table 2 and the graph in FIG. 1 demonstrate that among the lyophilized preparations produced with the same length of lyophilization time, the lyophilized preparations produced through the freezing and the reduced-pressure drying which were both performed under irradiation of an electromagnetic wave tend to have the lowest water content. This shows that the lyophilization can be efficiently performed through the freezing and the reduced-pressure drying which are both performed under irradiation of an electromagnetic wave and can achieve energy saving, low cost, and a reduction in processing time. Also, the quality of the preparations is effectively maintained.

Example 6

(Lyophilized Preparation Obtained by Lyophilization Under Irradiation of Electromagnetic Wave and Static Magnetic Field)

To purified water (989.9 parts by weight) was dissolved HPC-SSL (an excipient) (Nippon Soda Co., Ltd.) to prepare a 5% HPC-SSL solution. The solution was dispensed in 0.5-mL portions into plastic blister cases (Cryomold (0.5 mL, square), Sakura Finetek). The blister cases were arranged on a shelf plate in a lyophilization chamber. The solutions in each blister case were frozen at −60° C. under irradiation of an electromagnetic wave and a static magnetic field, dried at −10° C. and 1.5 Pa for 12 hours under irradiation of an electromagnetic wave and a static magnetic field (primary reduced-pressure drying), and then dried at 30° C. and 1.5 Pa for 4.5 hours under irradiation of an electromagnetic wave and a static magnetic field (secondary reduced-pressure drying). Thus, a lyophilized preparation was obtained. Each obtained lyophilized preparation portion was quickly put in a dry aluminum pouch and sealed with a heat sealer.

The lyophilization conditions in Example 6 are the same as the lyophilization conditions A in Example 1.

Examples 7 to 9

Lyophilized preparations were each obtained by the same procedure as in Example 6, except that the concentration and type of the excipient were changed according to the following Table 3. Each lyophilized preparation portion was put in a dry aluminum pouch and sealed with a heat sealer.
Dextran 70 (Meito Sangyo Co., Ltd.)

TABLE 2

| | Static magnetic field | | | |
|---|---|---|---|---|
| | OFF | OFF | OFF | OFF |
| | Electromagnetic wave | | | |
| | ON/ON | OFF/OFF | ON/OFF | OFF/ON |
| | Rh % | | | |
| Composition | 44 Water content (%) | 40 Water content (%) | 45 Water content (%) | 43 Water content (%) |
| 5% HPC-SSL | Example 1 1.0 | Comparative Example 1 1.3 | Comparative Example 6 1.0 | Comparative Example 11 1.1 |
| 5% Dextran | Example 2 3.2 | Comparative Example 2 3.6 | Comparative Example 7 3.7 | Comparative Example 12 3.2 |
| 10% Gelatin | Example 3 1.7 | Comparative Example 3 2.3 | Comparative Example 8 2.8 | Comparative Example 13 2.3 |
| 3% Pectin | Example 4 3.9 | Comparative Example 4 4.8 | Comparative Example 9 4.2 | Comparative Example 14 4.4 |
| 10% Dextran | Example 5 2.0 | Comparative Example 5 2.2 | Comparative Example 10 2.4 | Comparative Example 15 2.4 |

Gelatin (Nippi. Inc., product name: Nippi Gelatin SCF)
Pectin (Sansho Co., Ltd., distributed by: P Kelco Japan, product name: GENU pectin type LM-102AS-J)

Comparative Example 16

(Lyophilized Preparation Obtained by Lyophilization Under No Irradiation of Electromagnetic Wave or Static Magnetic Field)

A lyophilized preparation was obtained as in Example 6, except that the lyophilization was performed under no irradiation of an electromagnetic wave or a static magnetic field. Each lyophilized preparation portion was put in a dry aluminum pouch and sealed with a heat sealer.

Comparative Examples 17 to 19

Lyophilized preparations were each obtained by the same procedure as in Comparative Example 16, except that the concentration and type of the excipient were changed according to the following Table 3. Each lyophilized preparation portion was put in a dry aluminum pouch and sealed with a heat sealer.

Comparative Example 20

(Lyophilized Preparation Obtained Through Freezing Under Irradiation of Electromagnetic Wave and Static Magnetic Field)

A lyophilized preparation was obtained as in Example 6, except that the reduced-pressure drying was performed under no irradiation of an electromagnetic wave or a static magnetic field. Each lyophilized preparation portion was put in a dry aluminum pouch and sealed with a heat sealer.

Comparative Examples 21 to 23

Lyophilized preparations were each obtained by the same procedure as in Comparative Example 20, except that the concentration and type of the excipient were changed according to the following Table 3. Each lyophilized preparation portion was put in a dry aluminum pouch and sealed with a heat sealer.

Comparative Example 24

(Lyophilized Preparation Obtained Through Reduced-Pressure Drying Under Irradiation of Electromagnetic Wave and Static Magnetic Field)

A lyophilized preparation was obtained as in Example 6, except that the freezing was performed under no irradiation of an electromagnetic wave or a static magnetic field. The obtained lyophilized preparation was quickly put in a dry aluminum pouch and sealed with a heat sealer.

Comparative Examples 25 to 27

Lyophilized preparations were each obtained by the same procedure as in Comparative Example 24, except that the concentration and type of the excipient were changed according to the following Table 3. Each lyophilized preparation portion was put in a dry aluminum pouch and sealed with a heat sealer.

The lyophilized preparation was taken out from the aluminum pouch. The water content of the preparation was quickly determined using a Karl Fischer moisture meter. The weight percentage of the water relative to the weight of the preparation was determined as the water content (%) of the lyophilized preparation. The results are shown in Table 3 and the graph in FIG. 2.

TABLE 3

Application of electromagnetic wave and static magnetic field in freezing/
Application of electromagnetic wave and static magnetic field in reduced-pressure drying

| Composition | ON/ON Water content (%) | | OFF/OFF Water content (%) | | ON/OFF Water content (%) | | OFF/ON Water content (%) | |
|---|---|---|---|---|---|---|---|---|
| 5% HPC-SSL | Example 6 | 0.86 | Comparative Example 16 | 2.88 | Comparative Example 20 | 3.70 | Comparative Example 24 | 3.32 |
| 5% Dextran70 | Example 7 | 7.90 | Comparative Example 17 | 8.17 | Comparative Example 21 | 8.74 | Comparative Example 25 | 8.17 |
| 10% Gelatin | Example 8 | 2.95 | Comparative Example 18 | 3.56 | Comparative Example 22 | 6.81 | Comparative Example 26 | 6.40 |
| 3% Pectin | Example 9 | 5.16 | Comparative Example 19 | 7.74 | Comparative Example 23 | 8.82 | Comparative Example 27 | 8.12 |

Figure 2:
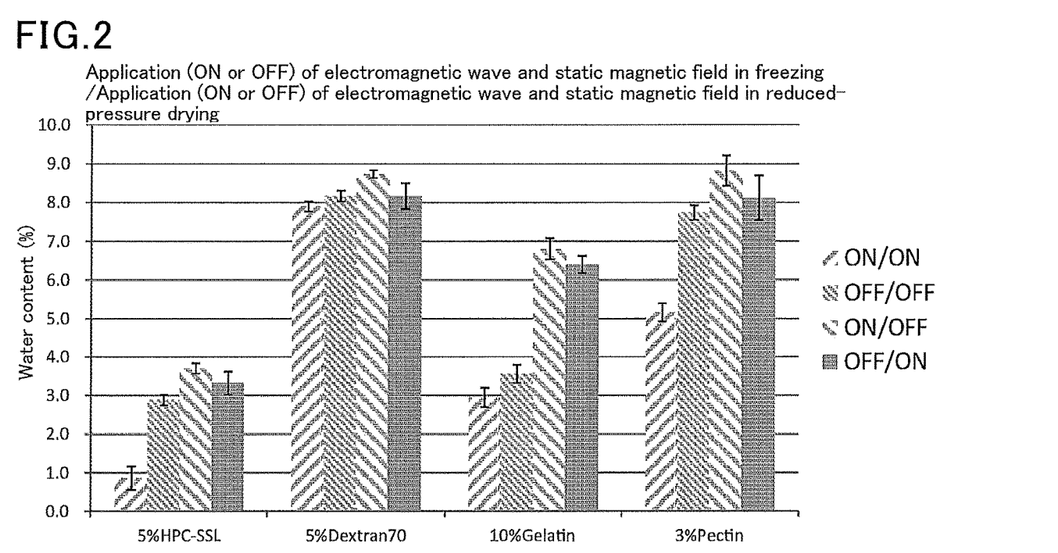
FIG. 2 is a graph visually showing a water content in Examples 6 to 9 and Comparative Examples 16 to 27.

The results shown in Table 3 and the graph of FIG. 2 demonstrate that the lyophilized preparations produced through the freezing and the reduced-pressure drying which were both performed under irradiation of a static magnetic field and an electromagnetic wave obviously have a lower water content than the lyophilized preparations (Comparative Examples 16 to 27) produced through the freezing and the reduced-pressure drying one or both of which were performed without irradiation of a static magnetic field and an electromagnetic wave. This shows that the lyophilization process under irradiation of an electromagnetic wave and a static magnetic field can achieve energy saving, low cost, and a reduction in processing time and can provide a preparation having advantages in stability and maintaining the quality.

Examples 10, 11, and 12

(Lyophilized Preparation Obtained by Lyophilization Under Irradiation of Electromagnetic Wave and Static Magnetic Field)

Lyophilized preparations (Examples 10 to 12) were obtained by the same procedure as in Example 6, except that the lyophilization conditions in Examples 10, 11, and 12 were respectively changed according to Table 1 (lyophilization conditions A), Table 4 (lyophilization conditions B), and Table 5 (lyophilization conditions C), Dextran 70 (Meito Sangyo Co., Ltd.) was used as an excipient, and a 10%

Dextran 70 solution was used. Each lyophilized preparation portion was put in a dry aluminum pouch and sealed with a heat sealer.

Comparative Examples 28, 29, and 30

(Lyophilized Preparation Obtained by Lyophilization Under No Irradiation of Electromagnetic Wave or Static Magnetic Field)

Lyophilized preparations (Comparative Examples 28 to 30) were obtained by the same procedure as in Comparative Example 16, except that the lyophilization conditions in Comparative Examples 28, 29, and 30 were respectively changed according to Table 1 (lyophilization conditions A), Table 4 (lyophilization conditions B), and Table 5 (lyophilization conditions C), Dextran 70 (Meito Sangyo Co., Ltd.) was used as an excipient, and a 10% Dextran 70 solution was used. Each lyophilized preparation portion was put in a dry aluminum pouch and sealed with a heat sealer.

The lyophilized preparation was taken out from the aluminum pouch. The water content of the preparation was quickly determined using a Karl Fischer moisture meter. The weight percentage of the water relative to the weight of the preparation was determined as the water content (%) of the lyophilized preparation.

The results are shown in Table 6.

TABLE 4

| Process | Temperature (° C.) | Time (hr) |
|---|---|---|
| Freezing | 25 | 0.5 |
| | 25 to −60 | 3 |
| | −60 | 0.5 |
| Primary reduced-pressure drying | −60 to −10 | 2.5 |
| | −10 | 6 |
| Secondary reduced-pressure drying | −10 to 30 | 1 |
| | 30 | 4.5 |

TABLE 5

| Process | Temperature (° C.) | Time (hr) |
|---|---|---|
| Freezing | 25 | 0.5 |
| | 25 to −60 | 3 |
| | −60 | 0.5 |
| Primary reduced-pressure drying | −60 to −10 | 2.5 |
| | −10 | 4 |
| Secondary reduced-pressure drying | −10 to 30 | 1 |
| | 30 | 4.5 | the primary reduced-pressure drying in Example 11 is half of that in Example 10, the water contents of the preparations in Examples 10 and 11 are nearly equal to each other. Despite the length of the time of the primary reduced-pressure drying in Example 12 is one third of that in Example 10, the water contents of the preparations in Examples 10 and 12 are nearly equal to each other. Comparing Comparative Examples 28 (lyophilization conditions A) and 29 (lyophilization conditions B) shows that when the length of time of the primary reduced-pressure drying is short, the water content is high.

This shows that the lyophilization process under irradiation of an electromagnetic wave and a static magnetic field can achieve energy saving, low cost, and a reduction in processing time and provide a preparation having advantages in stability and maintaining the quality.

Examples 13 to 17

(Lyophilized Preparation Obtained Through Very Short Time of Primary Reduced-Pressure Drying)

A 10% Dextran 70 solution was dispensed in 2.0-mL portions into plastic blister cases (Cryomold (2.0 mL, round), Sakura Finetek). The blister cases were arranged on a shelf plate in a lyophilization chamber. The solutions in each blister case were frozen at −60° C. under irradiation of an electromagnetic wave and a static magnetic field, dried at −10° C. and 1.5 Pa for four hours under irradiation of an electromagnetic wave and a static magnetic field (primary reduced-pressure drying), and then dried at 30° C. and 1.5 Pa for 4.5 hours under irradiation of an electromagnetic wave and a static magnetic field (secondary reduced-pressure drying). Thus, lyophilized preparations (Examples 13 to 17) were obtained. Each lyophilized preparation portion was quickly put in a dry aluminum pouch and sealed with a heat sealer.

The lyophilization conditions in Examples 13 to 17 are the same as the lyophilization conditions C in Example 12.

Test Examples 1 to 5

Lyophilized preparations (Test Examples 1 to 5) were obtained by the same procedure as in Examples 13 to 17, respectively, except that the freezing and the reduced-pressure drying were performed under no irradiation of a static

TABLE 6

| | | Example | | | Comparative Example | | |
|---|---|---|---|---|---|---|---|
| Composition | Lyophilization conditions | | Application of static magnetic field and electromagnetic wave | Water content (%) | | Application of static magnetic field and electromagnetic wave | Water content (%) |
| 10% Dextran70 | A | Example 10 | Applied | 1.8 | Comparative Example 28 | Not applied | 2.58 |
| 10% Dextran70 | B | Example 11 | Applied | 1.71 | Comparative Example 29 | Not applied | 4.65 |
| 10% Dextran70 | C | Example 12 | Applied | 1.44 | Comparative Example 30 | Not applied | Unmeasurable |

The results in Table 6 demonstrate that comparing Examples 10 and 11 shows that despite the length of time of magnetic field. Each lyophilized preparation portion was put in a dry aluminum pouch and sealed with a heat sealer.

The lyophilized preparation was taken out from the aluminum pouch. The water content of the preparation was quickly determined using a Karl Fischer moisture meter. The weight percentage of the water relative to the weight of the preparation was determined as the water content of the lyophilized preparation. The appearance of the lyophilized preparation taken out was observed from the upper surface and the lower surface.

The results are shown in Table 7.

TABLE 7

| | | Static magnetic field | | | |
|---|---|---|---|---|---|
| | | ON/ON | | OFF/OFF | |
| | | Electromagnetic wave | | | |
| | | ON/ON | | ON/ON | |
| Composition | | Water content (%) | Appearance | Water content (%) | Appearance |
| 10% Dextran70 | Example 13 | 1.4 | n = 3 slight depression is observed | Test Example 1 | 1.3 | n = 5 depression is observed in all test examples |
| | Example 14 | 1.2 | | Test Example 2 | 1.4 | |
| | Example 15 | 1.7 | | Test Example 3 | 1.4 | |
| | Example 16 | 1.6 | | Test Example 4 | 1.5 | |
| | Example 17 | 1.5 | | Test Example 5 | 1.6 | |
| | Average water content | 1.46 | | Average water content | 1.44 | |

The results in Table 7 demonstrate that even when the primary reduced-pressure drying time is shorter (the drying conditions in Examples 13 to 17 and Test Examples 1 to 5 are the same as those in Example 12, but the size of each of the preparations in Examples 13 to 17 and Test Examples 1 to 5 is four times the size of the preparation in Example 12), no significant change in water content was found when the freezing and the reduced-pressure drying were performed under irradiation of an electromagnetic wave. With regard to the appearance, in Examples 13 to 17 in which a static magnetic field was further applied in the freezing and the reduced-pressure drying, some of the preparations have a slight depression on their upper surface or lower surface, but are acceptable for appearance. On the other hand, in Test Examples 1 to 5, all the preparations have a depression on their upper surface or lower surface. These demonstrate that a very short time of the primary reduced-pressure drying is preferably performed under irradiation of an electromagnetic wave and a static magnetic field.

The ambient environmental humidity (Rh %) has a considerable influence on the results of water contents in the examples, comparative examples, and test examples. The effects and technical significance of the present invention can be fully understood by the difference between the presence and absence of an electromagnetic wave and/or a static magnetic field under the same conditions.

INDUSTRIAL APPLICABILITY

The present invention aims to provide a method and an apparatus for producing a lyophilized body, each of which can achieve energy saving, low cost, and a reduction in processing time and can provide a lyophilized body less damaged by a freezing process and a drying process.

The invention claimed is:

1. A method for producing a lyophilized body, comprising:
   freezing a substance to produce a frozen substance, which is a raw material of the lyophilized body, under irradiation of a first electromagnetic wave during a freezing stage; and
   reduced-pressure drying the frozen substance under irradiation of a second electromagnetic wave during a sublimation stage.

2. The method for producing a lyophilized body according to claim 1, further comprising:
   the freezing being performed under irradiation of the first electromagnetic wave and a first magnetic field, and the reduced-pressure drying being performed under irradiation of the second electromagnetic wave and a second magnetic field.

3. The method for producing a lyophilized body according to claim 1,
   wherein the reduced-pressure drying includes primary reduced-pressure drying and secondary reduced-pressure drying.

4. The method for producing a lyophilized body according to claim 2,
   wherein the first and second magnetic fields are static magnetic fields.

5. The method for producing a lyophilized body according to claim 1,
   wherein the substance is a drug-containing material containing water and at least one drug.

6. The method for producing a lyophilized body according to claim 5,
   wherein the at least one drug includes a protein.

7. The method for producing a lyophilized body according to claim 6,
   wherein the protein is a physiologically active protein.

8. The method for producing a lyophilized body according to claim 7, wherein the physiologically active protein is at least one selected from the group consisting of an antibody protein, an antigen protein, and an allergenic protein.

9. A lyophilizer for producing a lyophilized body, the lyophilizer comprising:
- a freezer configured to freeze a substance to produce a frozen substance, which is a raw material of the lyophilized body, during a freezing stage;
- a chamber configured to reduce an ambient pressure around the frozen substance during a sublimation stage; and
- an electromagnetic wave generator configured to generate an electromagnetic wave to be applied to the substance during both the freezing stage and the sublimation stage.

10. The lyophilizer according to claim 9, further comprising:
- a magnetic field generator configured to generate a magnetic field to be applied to the sub stance.

11. The lyophilizer according to claim 10, wherein the magnetic field generator is a static magnetic field generator configured to generate a static magnetic field.

12. The lyophilizer according to claim 9, wherein the electromagnetic wave generator comprises an electromagnetic wave oscillator, an amplifier, and an electromagnetic wave emitting antenna.

13. The method for producing a lyophilized body according to claim 1, wherein, during the freezing stage, the substance is irradiated under the irradiation of the first electromagnetic wave while lowering a temperature of the substance from room temperature to a freezing temperature.

14. The method for producing a lyophilized body according to claim 13, wherein the freezing temperature is from −40° Celsius to −70° Celsius.

15. The lyophilizer according to claim 9, wherein the chamber is a vacuum chamber.

* * * * *